(12) United States Patent
Jung et al.

(10) Patent No.: US 7,064,210 B2
(45) Date of Patent: Jun. 20, 2006

(54) LIGHT RESISTANT COLORANT AND COMPOSITION CONTAINING THE SAME

(75) Inventors: Yeon-kyoung Jung, Seoul (KR); Seung-min Ryu, Gyeonggi-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 10/672,062

(22) Filed: Sep. 29, 2003

(65) Prior Publication Data

US 2004/0129178 A1 Jul. 8, 2004

(30) Foreign Application Priority Data

Sep. 28, 2002 (KR) .................. 10-2002-0059138

(51) Int. Cl.
- *C07D 401/12* (2006.01)
- *C07C 245/10* (2006.01)
- *F21V 9/16* (2006.01)
- *C08K 5/3435* (2006.01)

(52) U.S. Cl. ............... 546/188; 534/560; 252/582; 106/493; 546/234; 546/231

(58) Field of Classification Search ............... 546/188, 546/231, 234; 252/582; 106/493; 534/560
See application file for complete search history.

(56) References Cited

U.S. PATENT DOCUMENTS 6,187,387 B1  2/2001  Bolle et al.

FOREIGN PATENT DOCUMENTS

CN  1237501 A  8/1999

OTHER PUBLICATIONS

China Office Action Jan. 7, 2005.

*Primary Examiner*—Charanjit S. Aulakh
(74) *Attorney, Agent, or Firm*—Staas & Halsey LLP

(57) ABSTRACT

A light resistant colorant is obtained by coupling a dye or a pigment with a light resistant material. A light resistant colorant-containing composition has no additional light stabilizer. Therefore, side effects caused by the addition of a light stabilizer, such as precipitate generation, may be prevented. Furthermore, substrates to which the composition is applied preserve excellent light resistance for a long term.

29 Claims, No Drawings

LIGHT RESISTANT COLORANT AND COMPOSITION CONTAINING THE SAME

CROSS-REFERENCE TO RELATED APPLICATIONS

This application claims the priority of Korean Patent Application No. 2002-59138, filed on Sep. 28, 2002, in the Korean Intellectual Property Office, the disclosure of which is incorporated herein in its entirety by reference.

BACKGROUND OF THE INVENTION

1. Field of the Invention

The present invention relates to a light resistant colorant and a composition containing the colorant. More particularly, the present invention relates to a light resistant colorant obtained by coupling a light resistant material with a dye or a pigment, and a composition containing the colorant.

2. Description of the Related Art

Generally, colorants are substances that develop their colors by selectively absorbing or reflecting visible light. Colorants are widely used in a variety of coloration industries, for example, in foods, drugs, cosmetics, paints, ink-jet inks, toners, fibers, leathers, plastics coloration, rubbers coloration, furniture fabrication, textile printing, paper-making, and ceramics. There are two types of colorants: dyes and pigments. Dyes are colored substances that are dissolved and mono-dispersed in water or oil and are bonded to molecules of substrates, such as fibers, for coloration. Pigments are not dissolved in water or oil, and thus, pigment powders form opaque colored films on the surfaces of substrates. Conventionally, dyes provide a wide color gamut and a bright and clear color. However, decoloration or discoloration by light and running of colors in water or organic solvents are likely to occur. Therefore, dyes have poor light and water resistance. On the other hand, pigments have better light and water resistance than dyes. However, when pigments are exposed to ultraviolet light from the sun or the like for a long time, they may become discolored. In addition, pigments provide a narrower color gamut and types of pigments are not diversified, relative to dyes. For these reasons, light stabilizers are separately added to compositions containing colorants in an attempt to improve light resistance of the compositions. However, such light stabilizers lower the stability of the compositions, thus generating precipitates. Therefore, it is difficult to ensure consistencies of the compositions. In addition, when the compositions are projected onto substrates through small-sized orifices, in particular, as in ink-jet printing, the orifices are easily clogged due to coagulation of the compositions.

SUMMARY OF THE INVENTION

The present invention provides a light resistant colorant. The light resistant colorant is prepared by coupling a common colorant with a light resistant material.

The present invention also provides a composition containing the light resistant colorant.

According to an aspect of the present invention, a light resistant colorant is obtained by coupling a common colorant with a light resistant material represented by Formula 1:

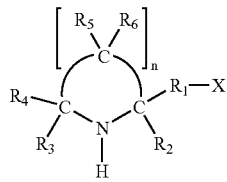

Formula 1 wherein $R_1$ is selected from the group consisting of a substituted or an unsubstituted alkylene of 1–20 carbon atoms, a substituted or an unsubstituted heteroalkylene of 1–20 carbon atoms, a substituted or an unsubstituted arylene of 6–20 carbon atoms, and a heteroarylene of 6–30 carbon atoms; $R_2$, $R_3$ and $R_4$ are independently selected from the group consisting of a hydrogen, a substituted or an unsubstituted alkyl of 1–4 carbon atoms, and a substituted or an unsubstituted heteroalkyl of 1–4 carbon atoms; $R_5$ and $R_6$ are independently selected from the group consisting of a hydrogen, an alkyl of 1–20 carbon atoms, a heteroalkyl of 1–20 carbon atoms, an aryl of 6–20 carbon atoms, or a heteroaryl of 6–20 carbon atoms; X is a halogen, a hydroxyl, an amino, carboxylic acid or a salt thereof, sulfonic acid or a salt thereof, and phosphoric acid or a salt thereof; and n is an integer of 1–5.

According to specific embodiments of the present invention, the light resistant material is a compound represented by Formula 2:

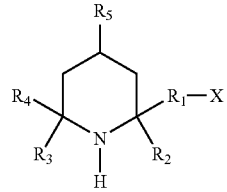

Formula 2 wherein $R_1$ is selected from the group consisting of a substituted or an unsubstituted alkylene of 1–20 carbon atoms, a substituted or an unsubstituted heteroalkylene of 1–20 carbon atoms, a substituted or an unsubstituted arylene of 6–20 carbon atoms, and a heteroarylene of 6–30 carbon atoms; $R_2$, $R_3$ and $R_4$ are independently selected from the group consisting of a hydrogen, a substituted or unsubstituted alkyl of 1–4 carbon atoms, and a substituted or unsubstituted heteroalkyl of 1–4 carbon atoms; $R_5$ is selected from the group consisting of a hydrogen, an alkyl of 1–20 carbon atoms, a heteroalkyl of 1–20 carbon atoms, an aryl of 6–20 carbon atoms, and a heteroaryl of 6–20 carbon atoms; and X is selected from the group consisting of a halogen, a hydroxyl, an amino, carboxylic acid or a salt thereof, sulfonic acid or a salt thereof, phosphoric acid or a salt thereof.

The common colorant and the light resistant material are coupled with each other via an amine bond, an ester bond, or an amide bond.

The common colorant may be a dye or a pigment.

The light resistant colorant may be used in a variety of coloration industries such as in toners, paints, ink-jet inks, coatings, fibers, leathers, plastics coloration, rubbers coloration, furniture fabrication, textile printing, paper-making, and ceramics.

According to another aspect of the present invention, a composition may comprise the light resistant colorant of Formula 1, a carrier medium, and/or an additive.

The carrier medium may be water, one or more organic solvents, or a mixture thereof.

When the carrier medium is a mixture of water with one or more organic solvents, the organic solvent may be added to the composition in an amount of 5 to 50 parts by weight based on 100 parts by weight of the composition.

The organic solvent may be an alcohol such as methyl alcohol, ethyl alcohol, n-propyl alcohol, isopropyl alcohol, n-butyl alcohol, sec-butyl alcohol, t-butyl alcohol, and isobutyl alcohol; ketones such as acetone, methyl ethyl ketone, and diacetone alcohol; an ester such as ethyl acetate and ethyl lactate; a polyhydric alcohol such as ethyleneglycol, diethyleneglycol, triethyleneglycol, propyleneglycol, butyleneglycol, 1,4-butanediol, 1,2,4-butanetriol, 1,5-pentanediol, 1,2,6-hexanetriol, hexyleneglycol, glycerol, glycerol ethoxylate, and trimethylolpropane ethoxylate; a lower alkyl ether such as ethyleneglycol monomethyl ether, ethyleneglycol monoethyl ether, diethyleneglycol methyl ether, diethyleneglycol ethyl ether, triethyleneglycol monomethyl ether, and triethyleneglycol monoethyl ether; a nitrogen-containing compound such as 2-pyrrolidone and N-methyl-2-pyrrolidone; or a sulfur-containing compound such as dimethyl sulfoxide, tetramethylenesulfone and thioglycol.

The additive may be a dispersing agent, a surfactant, a wetting agent, a viscosity modifier, a penetrant, a pH-adjustor, and/or a metal oxide.

Additional aspects and advantages of the invention will be set forth in part in the description which follows and, in part, will be obvious from the description, or may be learned by practice of the invention.

DETAILED DESCRIPTION OF THE EMBODIMENTS

Reference will now be made in detail to the present embodiments of the present invention.

A light resistant colorant of the present invention is formed by coupling a common colorant with a light resistant material. In detail, the light resistant colorant may be obtained via the formation of an amine bond, an ester bond or an amide bond between a light-resistant, hindered amine derivative and one or more amino groups, hydroxyl groups, carboxyl groups, or sulfonic acid groups of a dye or a pigment.

The light resistant colorant of the present invention is prepared via the formation of an amine bond, an ester bond, or an amide bond between the light resistant material of Formula 1 and an amino, a hydroxyl, or a carboxyl group of a common colorant, as represented in Schemes 1–3:

Scheme 1

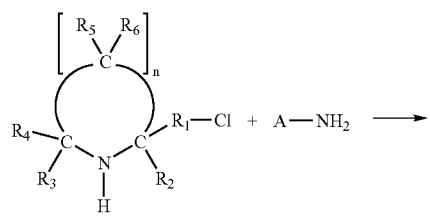

-continued

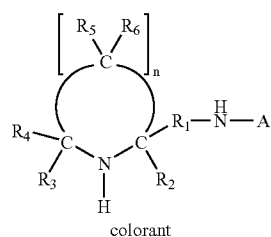
colorant wherein, $R_1$, $R_2$, $R_3$, $R_4$, $R_5$ and $R_6$ are the same as defined above.

Scheme 2

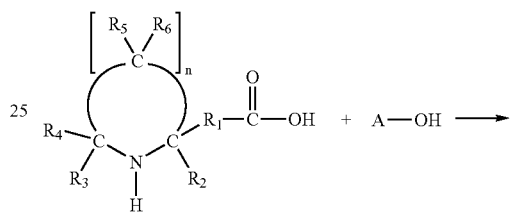

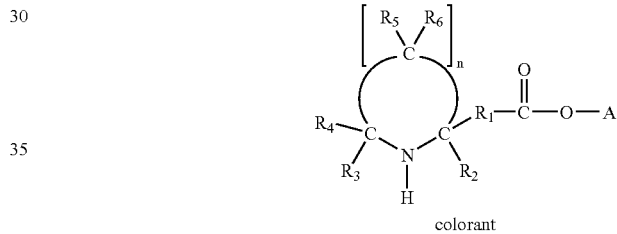
colorant wherein, $R_1$, $R_2$, $R_3$, $R_4$, $R_5$ and $R_6$ are the same as defined above.

Scheme 3

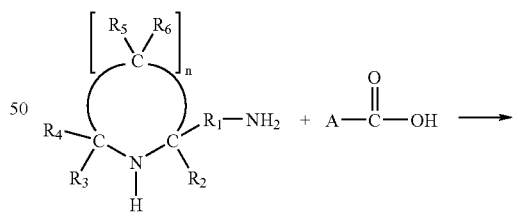

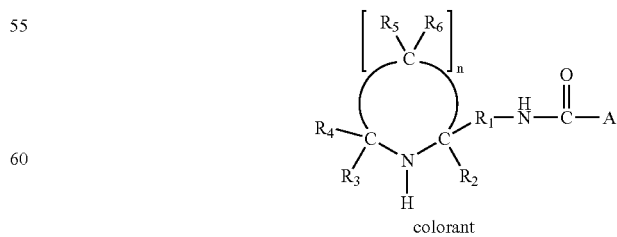
colorant wherein, $R_1$, $R_2$, $R_3$, $R_4$, $R_5$ and $R_6$ are the same as defined above.

A common colorant to be coupled with the light resistant material may be any dye or pigment conventionally used in a variety of coloration industries such as in toners, inks, fibers, paints, and plastics coloration provided that an amino, a carboxyl, a hydroxyl or an amine group is present in a molecule of the dye or the pigment. Examples of the dye include, but are not limited to, C.I. Direct Black 9, 17, 19, 22, 32, 51, 56, 91, 94, 97, 166, 168, 173, and 199; C.I. Direct Blue 1, 10, 15, 22, 77, 78, 80, 200, 201, 202, 203, 207, and 211; C.I. Direct Red 2, 4, 9, 23, 31, 39, 63, 72, 83, 84, 89, 111, 173, 177, 184, and 240; and C.I. Direct Yellow 8, 9, 11, 12, 27, 28, 29, 33, 35, 39, 41, 44, 50, 53, and 58. Examples of the pigment include, but are not limited to, anthraquinone, phthalocyanine blue, phthalocyanine green, diazo, monoazo, pyranthrone, perylene, quinacridone, and an indigoid pigment.

The term, "alkylene", as used herein, refers to a divalent straight or branched chain group obtained as a result of removal of two hydrogen atoms from both ends of a normal paraffin based hydrocarbon. Generally, the alkylene has 1–20 carbon atoms, and preferably 1–12 carbon atoms. A lower alkylene having 1–6 carbon atoms is more preferable. One or more hydrogen atoms on the alkylene may be substituted with a halogen, a hydroxyl, a nitro, a cyano, an amino, an amidino, a hydrazine, a hydrazone, carboxylic acid or a salt thereof, sulfonic acid or a salt thereof, or phosphoric acid or a salt thereof.

The term, "heteroalkylene", as used herein, refers to a straight or branched chain group containing nitrogen (N), sulfur (S), oxygen (O) or phosphorus (P) in the alkylene as defined above. One or more hydrogen atoms on the heteroalkylene may be substituted with a halogen, a hydroxyl, a nitro, a cyano, an amino, an amidino, a hydrazine, a hydrazone, carboxylic acid or a salt thereof, sulfonic acid or a salt thereof, or phosphoric acid or a salt thereof.

The term, "arylene", as used herein, refers to a divalent aromatic hydrocarbon of 6–20 carbon atoms containing one or more rings. The arylene may have one to three substituted groups selected from the group consisting of a hydroxyl, a halogen, a haloalkyl, a nitro, a cyano, an alkoxy and a lower alkylamino.

The term, "heteroarylene", as used herein, refers to a divalent aromatic hydrocarbon of 6–20 carbon atoms containing N, S, O or P.

The term, "alkyl", as used herein, refers to a straight or branched chain group of 1–20 carbon atoms, preferably 1–12 carbon atoms, and more preferably 1–6 carbon atoms. Examples of the alkyl include methyl, ethyl, n-propyl, isopropyl, n-butyl, isobutyl, sec-butyl, t-butyl, pentyl, isoamyl and hexyl. A lower alkyl of 1–3 carbon atoms is more preferable. One or more hydrogen atoms on the alkyl may be substituted with a halogen, a hydroxyl, a nitro, a cyano, an amino, an amidino, a hydrazine, a hydrazone, carboxylic acid or a salt thereof, sulfonic acid or a salt thereof, or phosphoric acid or a salt thereof.

The term, "heteroalkyl", as used herein, refers to a straight or branched chain group containing N, S or O alkyl as defined above. Examples of the heteroalkyl include hydroxymethyl, acetoxymethyl, 3-hydroxypropyl, 1,2-dihydroxyethyl, 2-methoxyethyl, 2-aminoethyl, 2-dimethylaminoethyl, 2-acetylaminoethyl and 3-(pyrrolidin-1-yl)ethyl.

The present invention also provides a composition containing the above-described light resistant colorant obtained by coupling a common colorant with a light resistant material. The light resistant colorant-containing composition of the present invention has excellent light resistance even in the absence of a light stabilizer for enhancement of light resistance. Also, side effects caused by the addition of a light stabilizer to a conventional colorant-containing composition are prevented. That is, lowering of composition stability and precipitate generation are prevented. In particular, when the light resistant colorant-containing composition of the present invention is projected onto a substrate through a small-sized orifice, clogging of the orifice by composition coagulation occurs infrequently. Therefore, a substrate to which the light resistant colorant-containing composition of the present invention is applied may preserve excellent light resistance for a long term.

The light resistant colorant of the present invention may be used in a variety of coloration industries, for example, in toners, paints, ink-jet inks, coatings, fibers, leathers, plastics coloration, rubbers coloration, textile printing, paper-making, and ceramics. Hereinafter, an ink composition, as an illustrative embodiment of the light resistant colorant-containing composition, will be described in detail, but the present invention is not limited thereto.

The ink composition of the present invention comprises the light resistant colorant of Formula 1, a carrier medium, and/or an additive.

The light resistant colorant is added to the ink composition in an amount of 1 to 20 parts by weight based on 100 parts by weight of the ink composition.

The carrier medium may be water, one or more organic solvents, or a mixture thereof. When the carrier medium is a mixture of water with one or more organic solvents, the content of the organic solvent is 5 to 50 parts by weight based on 100 parts by weight of the ink composition.

The contents of the water and the organic solvent depend on various factors, for example, the viscosity, the surface tension, and the drying speed of the ink composition. The contents may also vary depending on a printing method and type of a substrate on which the ink is printed.

Examples of the organic solvent mainly used in the carrier medium include alcohols such as methyl alcohol, ethyl alcohol, n-propyl alcohol, isopropyl alcohol, n-butyl alcohol, sec-butyl alcohol, t-butyl alcohol, and isobutyl alcohol; ketones such as acetone, methylethyl ketone, and diacetone alcohol; an ester such as ethyl acetate and ethyl lactate; a polyhydric alcohol such as ethyleneglycol, diethyleneglycol, triethyleneglycol, propyleneglycol, butyleneglycol, 1,4-butanediol, 1,2,4-butanetriol, 1,5-pentanediol, 1,2,6-hexanetriol, hexyleneglycol, glycerol, glycerol ethoxylate, and trimethylolpropane ethoxylate; a lower alkyl ether such as ethyleneglycol monomethyl ether, ethyleneglycol monoethyl ether, diethyleneglycol methyl ether, diethyleneglycol ethyl ether, triethyleneglycol monomethyl ether, and triethyleneglycol monoethyl ether; a nitrogen-containing compound such as 2-pyrrolidone and N-methyl-2-pyrrolidone; and a sulfur-containing compound such as dimethyl sulfoxide, tetramethylenesulfone and thioglycol.

The additive may be a dispersing agent, a viscosity modifier, a surfactant, a wetting agent, a penetrant, a pH-adjustor, a metal oxide, a storage stabilizing material, or the like.

The dispersing agent is added to the ink composition to secure the dispersion stability of the light resistant colorant. When needed, one or more dispersing agents may be used. However, there are no particular limitations on the dispersing agent. In this regard, in addition to dispersing agents with a simple structure and a low molecular weight, high molecular weight dispersing agents such as a block copolymer may also be used herein.

Examples of dispersing agents with a relatively lower molecular weight and a simple structure include, but are not limited to, polyvinylalcohol (PVA), cellulosics, ethylene oxide modified phenol, ethylene oxide/propylene oxide polymer, a sodium polyacrylate solution (TEGO, disperse 715W), a modified polyacryl resin solution (TEGO, disperse 735W), solution of an alkylol ammonium salt of a low molecular weight polycarboxylic acid polymer (BYK-Chemie, Disperbyk), solution of an alkylol ammonium salt of polyfunctional polymer (BYK-Chemie, Disperbyk-181) or a mixture thereof.

On the other hand, a siloxane based copolymer such as polyether siloxane copolymer (TEGO, Wet KL 245/Wet 260) and a "AB" or "BAB" based structural polymer may be used as dispersing agents with a relatively higher molecular weight and a complex structure. "A", as used herein refers to a hydrophobic homopolymer or a copolymer of a substituted or an unsubstituted acrylic monomer of 1–30 carbon atoms. "B", as used herein, refers to a hydrophilic polymer or a copolymer of a substituted or an unsubstituted acrylic monomer of 1–30 carbon atoms. Examples of the structural polymer include, but are not limited to, acrylic acid/acrylate copolymer, methacrylic acid/methacrylate copolymer, acrylic acid/polydialkylsiloxane/acrylate block copolymer, and a mixture thereof.

Preferably, the content of the dispersing agent is 1 to 20 parts by weight based on 100 parts by weight of the ink composition.

The viscosity modifier acts to modify viscosity in order to maintain smooth jetting of the ink. Examples of the viscosity modifier include casein and carboxymethylcellulose. The viscosity modifier is added to the ink composition in an amount of 0.1 to 5.0 parts by weight based on 100 parts by weight of the ink composition.

The surfactant acts to stabilize the jetting performance of the ink from a nozzle by adjusting the surface tension of the ink composition. An anionic, a cationic, or a non-ionic surfactant may be used.

Examples of the anionic surfactant include an alkylcarboxylic acid salt of 1–1,000 carbon atoms, and preferably, an alkylcarboxylic acid salt of 10–200 carbon atoms, an alcohol sulfonic acid ester salt of 1–1,000 carbon atoms, and preferably, an alcohol sulfonic acid ester salt of 10–200 carbon atoms, an alkylsulfonic acid salt of 1–1,000 carbon atoms, and preferably, an alkylsulfonic acid salt of 10–200 carbon atoms, an alkylbenzenesulfonic acid salt of 1–1,000 carbon atoms, and preferably, an alkylbenzenesulfonic acid salt of 10–200 carbon atoms and a mixture thereof. Examples of the cationic surfactant include fatty acid amine salt, quarternary ammonium salt, sulfonium salt, phosphonium, and a mixture thereof. Examples of the non-ionic surfactant include polyoxyethylene alkyl ether in which the alkyl moiety has 1–1,000 carbon atoms, and preferably, 10–200 carbon atoms, polyoxyethylene alkyl phenyl ether in which the alkyl moiety has 1–1,000 carbon atoms, and preferably, 10–200 carbon atoms, polyoxyethylene secondary alcohol ether, polyoxyethylene-oxypropylene block copolymer, polyglycerine fatty acid ester, sorbitan fatty acid ester, and a mixture thereof. The surfactant is added to the ink composition in an amount of 0.1 to 5 parts by weight based on 100 parts by weight of the ink composition.

The wetting agent is used to prevent clogging of a nozzle. Examples of the wetting agent include a polyhydric alcohol such as glycerine, ethylene glycol, diethylene glycol, triethylene glycol, propylene glycol, dipropylene glycol, hexylene glycol, 1,3-butanediol, 1,4-butanediol, 1,5-pentanediol, 2-buten-1,4-diol, 2-methyl-2-pentanediol and a mixture thereof. The wetting agent is added to the ink composition in an amount of 10 to 30 parts by weight based on 100 parts by weight of the ink composition.

The composition of the present invention may be prepared using the components as mentioned above and the following procedure.

First, the above-described light resistant colorant is added to a carrier medium, and, if necessary, additives such as a dispersing agent, a viscosity modifier, and a surfactant are added thereto and mixed. The obtained mixture is thoroughly stirred in an agitator until a homogeneous mixture is obtained. Then, the homogeneous mixture is filtered through a filter with a pore size of 0.45 to 1.0 μm to prepare the ink composition of the present invention.

Hereinafter, the present invention will be described with reference to the following examples but is not limited thereto.

EXAMPLE 1

Preparation of Light Resistant Colorant 100 ml of DMSO and 13.0 g of a hindered amine derivative of Formula 3 were dissolved in a 250 ml Erlenmeyer flask. 28.7 g of C.I. Direct Black 51 was added and reacted at 120° C. for 8 hours. The resultant was then concentrated. The concentrate was dissolved in ether, and the resultant was washed with distilled water several times to separate an ether layer. Then, the ether layer was concentrated to yield 21.1 g of a light resistant colorant of Formula 4.

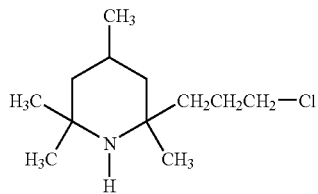

Formula 3

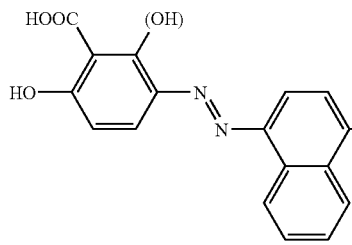

Formula 4

EXAMPLE 2

Preparation of Light Resistant Colorant 150 ml of ethyl acetate, 12.9 g of a hindered amine derivative of Formula 5, and 26.5 g of C.I. Direct Black 168 were dissolved in a 250 ml flask having a round-shaped bottom. One or two boiling chips were added, and 10 ml of a concentrated sulfuric acid was slowly added. The resultant mixture was thoroughly refluxed for 12 hours and washed with distilled water to separate an organic layer. Then, the organic layer was concentrated and recrystallized to yield 20.3 g of a light resistant colorant of Formula 6.

EXAMPLE 3

Preparation of Light Resistant Colorant 50 ml of DMSO and 19.1 g of a hindered amine derivative of Formula 5 were dissolved in a 250 ml Erlenmeyer flask. 7.0 g of $SOCl_2$ was added, and the resultant mixture was reacted at room temperature for 1 hour to produce a solution (A). A solution of 24.8 g of C.I. Pigment Red 177 in 100 ml DMSO was added to the solution (A). Then, one or two boiling chips were placed in the flask, and the flask was connected to a refluxing condenser. The resultant mixture was then allowed to react at 80° C. for 6 hours. The resultant

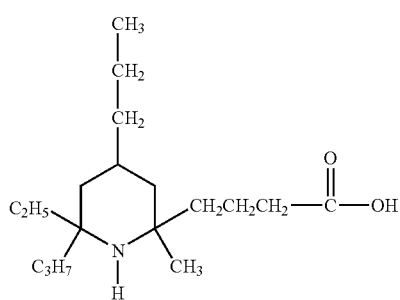

Formula 5

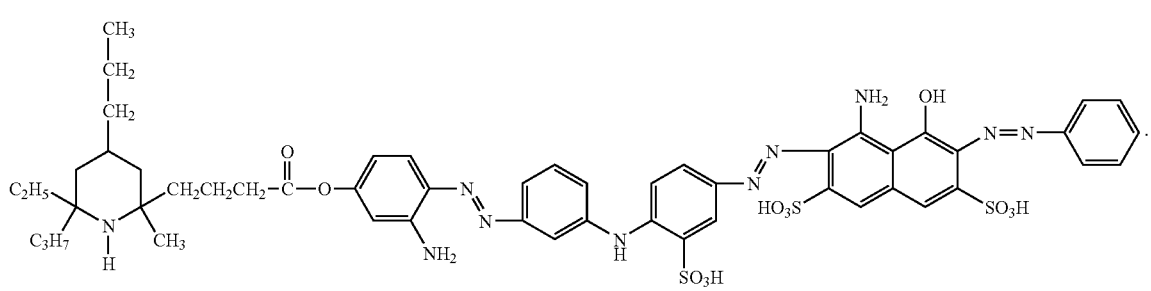

Formula 6 solution was cooled to room temperature, and excess methanol was added. As a result, crystals were obtained. The resulting crystals were collected using a suction filter. To remove unreacted substances, the crystals were dissolved in DMSO, and methanol was added. The obtained mixture was filtered through a suction filter to obtain final crystals. The final crystals were dried in an oven to yield 22.6 g of a light resistant colorant of Formula 7.

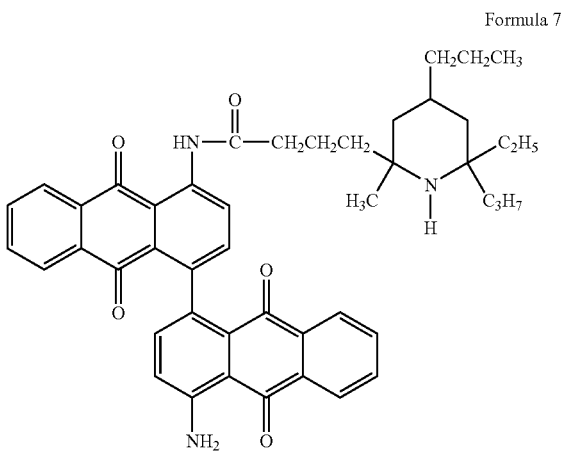

Formula 7

EXAMPLE 4

Preparation of Light Resistant Colorant 50 ml of DMSO and 15.2 g of a hindered amine derivative of Formula 8 were dissolved in a 250 ml Erlenmeyer flask. 5.7 g of $SOCl_2$ was added, and the mixture was reacted at room temperature for 1 hour to produce a solution (A). A solution of 28.6 g of C.I. Food Black 2 in 100 ml DMSO was added to the solution (A). Then, one or two boiling chips were placed in the flask, and the flask was connected to a refluxing condenser. The resultant mixture was then allowed to react at 80° C. for 6 hours. The resultant solution was cooled to room temperature, and excess methanol was added. As a result, crystals were obtained. The crystals were collected using a suction filter. To remove unreacted substances, the crystals were dissolved in DMSO, and methanol was added. The obtained mixture was filtered using a suction filter to obtain final crystals. The final crystals were dried in an oven to yield 23.4 g of a light resistant colorant of Formula 9.

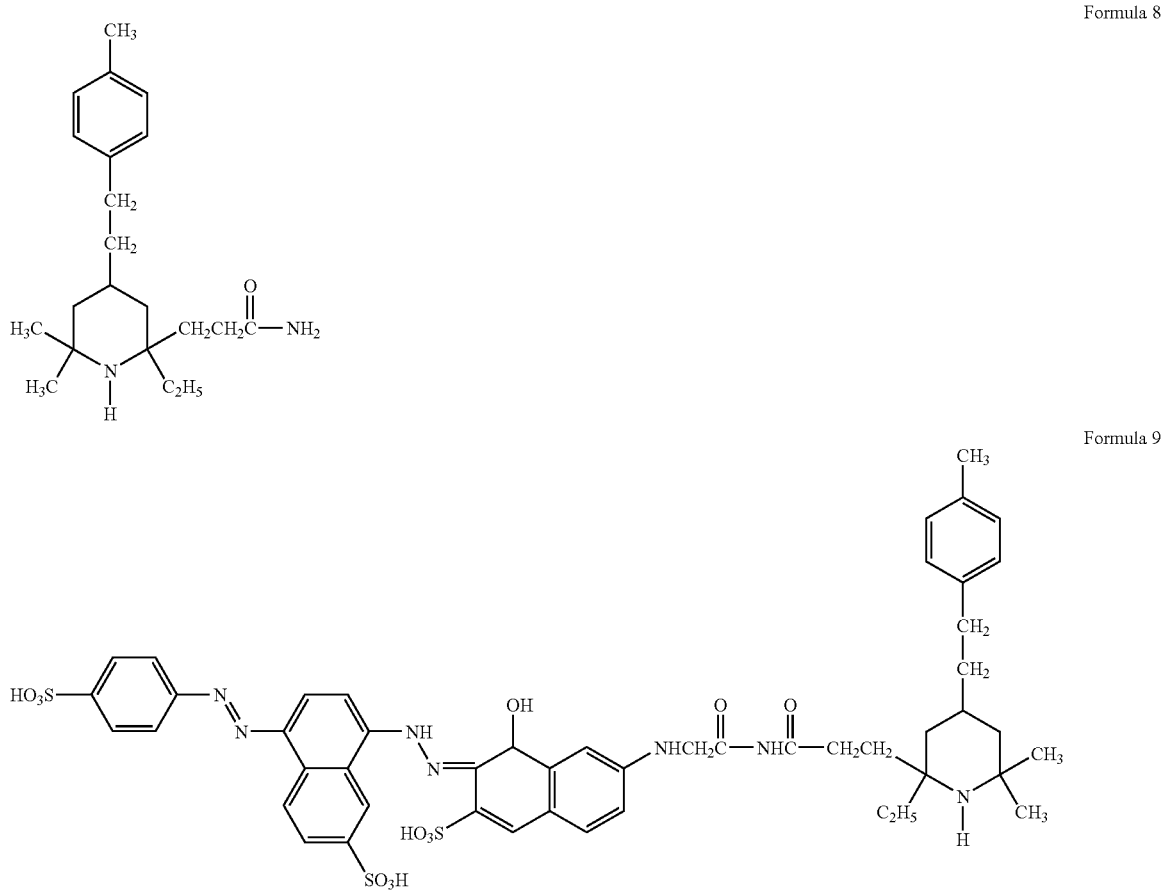

Formula 8

Formula 9

EXAMPLE 5

Preparation of Light Resistant Colorant 25.1 g of a light resistant colorant of Formula 11 was prepared in the same manner as in Example 1, except for using 23.4 g of a hindered amine derivative of Formula 10 and 19.9 g of C.I. Direct Black 168.

Formula 10

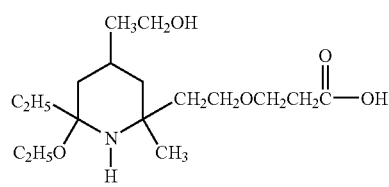

Formula 11

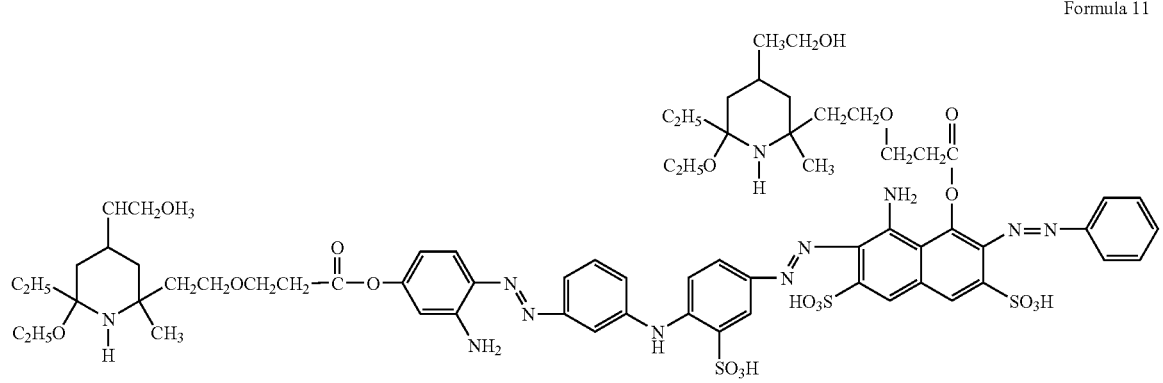

EXAMPLE 6

Preparation of Light Resistant Colorant 18.3 g of a light resistant colorant of Formula 13 was prepared in the same manner as in Example 1, except for using 15.8 g of a hindered amine derivative of Formula 12 and 20.7 g of C.I. Pigment Red 177.

Formula 12

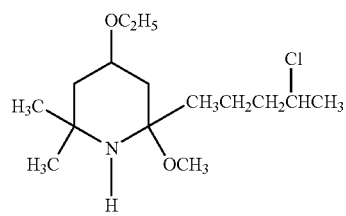

-continued

Formula 13

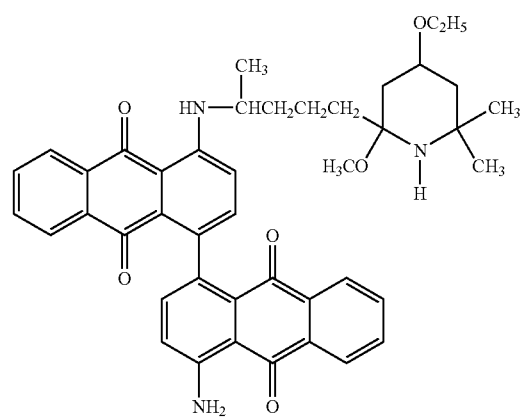

EXAMPLE 7

Preparation of Composition

| Component | Content |
|---|---|
| Light resistant colorant of Formula 4 prepared in Example 1 | 4.0 g |

| Component | Content |
| --- | --- |
| Water | 78.0 g |
| Isopropyl alcohol | 3.0 g |
| Ethylene glycol | 10.0 g |
| Glycerine | 5.0 g |

All the components were thoroughly mixed under stirring for 30 minutes or more to produce a homogeneous mixture. The resultant mixture was filtered through a filter with a pore size of 0.45 μm to prepare a desired composition of the present invention.

EXAMPLE 8

Preparation of Composition

A composition was prepared in the same manner as in Example 7, except for using the light resistant colorant of Formula 6 prepared in Example 2 instead of the light resistant colorant of Formula 4.

EXAMPLE 9

Preparation of Ink Composition

A composition was prepared in the same manner as in Example 7, except for using the light resistant colorant of Formula 7 prepared in Example 3, 3.0 g of TEGO disperse 750 W as a dispersing agent, 75.0 g of water, and a filter with a pore size of 0.8 μm.

EXAMPLE 10

Preparation of Ink Composition

A composition was prepared in the same manner as in Example 7, except for using the light resistant colorant of Formula 9 prepared in Example 4 instead of the light resistant colorant of Formula 4.

EXAMPLE 11

Preparation of Ink Composition

A composition was prepared in the same manner as in Example 7, except for using the light resistant colorant of Formula 11 prepared in Example 5 instead of the light resistant colorant of Formula 4.

EXAMPLE 12

Preparation of Ink Composition

A composition was prepared in the same manner as in Example 9, except for using the light resistant colorant of Formula 13 prepared in Example 6 instead of the light resistant colorant of Formula 4.

COMPARATIVE EXAMPLE 1

A composition was prepared in the same manner as in Example 7, except for using C.I. Direct Black 51 derivative instead of the light resistant colorant of Formula 4.

COMPARATIVE EXAMPLE 2

A composition was prepared in the same manner as in Example 8, except for using C.I. Direct Black 168 instead of the light resistant colorant of Formula 6.

COMPARATIVE EXAMPLE 3

A composition was prepared in the same manner as in Example 9, except for using C.I. Pigment Red 177 instead of the light resistant colorant of Formula 7.

COMPARATIVE EXAMPLE 4

A composition was prepared in the same manner as in Example 10, except for using C.I. Food Black 2 instead of the light resistant colorant of Formula 9.

COMPARATIVE EXAMPLE 5

A composition was prepared in the same manner as in Example 7, except for using C.I. Direct Black 51 derivative instead of the light resistant colorant of Formula 4, and separately adding 0.5% by weight of Irganox 245DW (a product of CIBA CO.) as a light stabilizer. In this case, the amount of water was reduced as much as the amount of the separately added light stabilizer.

COMPARATIVE EXAMPLE 6

A composition was prepared in the same manner as in Example 8, except for using C.I. Direct Black 168 instead of the light resistant colorant of Formula 6, and separately adding 0.5% by weight of Irganox 245DW (a product of CIBA CO.) as a light stabilizer. In this case, the amount of water was reduced as much as the amount of the separately added light stabilizer.

COMPARATIVE EXAMPLE 7

A composition was prepared in the same manner as in Example 9, except for using C.I. Pigment Red 177 instead of the light resistant colorant of Formula 7, and separately adding 0.5% by weight of Irganox 245DW (a product of CIBA CO.) as a light stabilizer. In this case, the amount of water was reduced as much as the amount of the separately added light stabilizer.

COMPARATIVE EXAMPLE 8

A composition was prepared in the same manner as in Example 10 except for using C.I. Food Black 2 instead of the light resistant colorant of Formula 9, and separately adding 0.5% by weight of Irganox 245DW (a product of CIBA CO.)

as a light stabilizer. In this case, the amount of water was reduced as much as that of the separately added light stabilizer.

Properties of compositions of Examples 7–12 and Comparative examples 1–8 were measured according to the following method.

EXPERIMENT 1

Long-term storage stability 100 ml of each of the compositions of Examples 7–12 and Comparative examples 1–8 was placed in a thermostable glass bottle, sealed, and allowed to stand in a 60° C. thermostatic bath. After two months, whether a precipitate was present or not was observed, and the results are presented in Table 1 below.

TABLE 1

| Section | Ex. 7 | Ex. 8 | Ex. 9 | Ex. 10 | Ex. 11 | Ex. 12 | Com. 1 | Com. 2 | Com. 3 | Com. 4 | Com. 5 | Com. 6 | Com. 7 | Com. 8 |
|---|---|---|---|---|---|---|---|---|---|---|---|---|---|---|
| Storage stability | ○ | ○ | ○ | ○ | ○ | ○ | ○ | ○ | ○ | ○ | X | X | X | X |

Ex.: Example,
Com.: Comparative example,
○: no precipitates,
X: precipitates

EXPERIMENT 2

Light resistance property

Each composition of Examples 7–12 and Comparative examples 1–8 was placed in an ink cartridge (SAMSUNG ELECTRONICS CO., LTD., Korea) and a solid pattern of 2 cm×2 cm was printed. The printed pattern was exposed to light in a Q-SUN xenon test chamber for 100 hours. OD values before and after testing were measured, and the OD value variation was evaluated using the following equation. The results are presented in Table 2 below.

$$A = OD(\text{after test})/OD(\text{before test}) \times 100(\%)$$

TABLE 2

| Section | Ex. 7 | Ex. 8 | Ex. 9 | Ex. 10 | Ex. 11 | Ex. 12 | Com. 1 | Com. 2 | Com. 3 | Com. 4 | Com. 5 | Com. 6 | Com. 7 | Com. 8 |
|---|---|---|---|---|---|---|---|---|---|---|---|---|---|---|
| Light resistance | ○ | ○ | ○ | ○ | ○ | ○ | X | X | Δ | X | Δ | ○ | ○ | Δ |

Ex.: Example,
Com.: Comparative example,
○: $A \geq 90$,
Δ: $75 \leq A < 90$,
X: $A < 75$ Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A light resistant colorant obtained by coupling a colorant having at least one functional group selected from the group consisting of amino groups, hydroxyl groups caroxyl groups, and sulfonic acid groups with a compound represented by Formula 2:

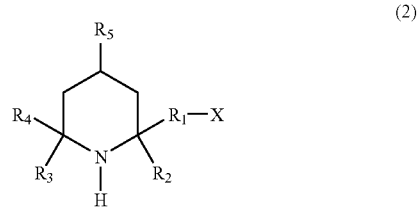

wherein $R_1$ is selected from the group consisting of a substituted or an unsubstituted alkylene of 1–20 carbon atoms and a substituted or an unsubstituted heteroalkylene of 1–20 carbon atoms; $R_2$, $R_3$ and $R_4$ are independently selected from the group consisting of a hydrogen, a substituted or an unsubstituted alkyl of 1–4 carbon atoms, and a substituted or an unsubstituted heteroalkyl of 1–4 carbon atoms; $R_5$ is selected from the group consisting of a hydrogen, an alkyl of 1–20 carbon atoms, a heteroalkyl of 1–20 carbon atoms, an aryl of 6–20 carbon atoms, and a heteroaryl of 6–20 carbon atoms; and X is selected from the group consisting of a halogen, a hydroxyl, an amino, carboxylic acid or a salt thereof, sulfonic acid or a salt thereof, and phosphoric acid or a salt thereof.

2. The light resistant colorant according to claim 1, wherein the colorant is a dye or a pigment.

3. A composition comprising:

the light resistant colorant according to claim 1; and
a carrier medium.

4. The composition according to claim 3, wherein the carrier medium is one of: water, at least one organic solvent, and a mixture thereof.

5. The composition according to claim 3, wherein, when the carrier medium is a mixture of water with at least one organic solvent, the organic solvent is added to the composition in an amount of 5 to 50 parts by weight based on 100 parts by weight of the composition.

6. The composition according to claim 4, wherein the organic solvent is selected from the group consisting of alcohols, ketones, esters, polyhydric alcohols, lower alkyl ethers, nitrogen-containing compounds, and sulfur-containing compounds.

7. The composition according to claim 3, further comprising at least one selected from the group consisting of a dispersing agent, a viscosity modifier, a surfactant, a wetting agent, a penetrant, a pH-adjustor, and a metal oxide.

8. A composition comprising:
the light resistant colorant according to claim 2; and
a carrier medium.

9. The composition according to claim 5, wherein the organic solvent is selected from the group consisting of alcohols, ketones, esters, polyhydric alcohols, lower alkyl ethers, nitrogen-containing compounds, and sulfur-containing compounds.

10. The composition according to claim 6, wherein the alcohol/alcohols is/are selected from the group consisting of methyl alcohol, ethyl alcohol, n-propyl alcohol, isopropyl alcohol, n-butyl alcohol, sec-butyl alcohol, t-butyl alcohol, and isobutyl alcohol.

11. The composition according to claim 6, wherein the ketone/ketones is/are selected from the group consisting of acetone, methylethyl ketone, and diacetone alcohol.

12. The composition according to claim 6, wherein the ester/esters is/are selected from the group consisting of ethyl acetate and ethyl lactate.

13. The composition according to claim 6, wherein the polyhydric alcohol/polyhydric alcohols is/are selected from the group consisting of ethyleneglycol, diethyleneglycol, triethyleneglycol, propyleneglycol, butyleneglycol, 1,4-butanediol, 1,2,4-butanetriol, 1,5-pentanediol, 1,2,6-hexanetriol, hexyleneglycol, glycerol, glycerol ethoxylate, and trimethylolpropane ethoxylate.

14. The composition according to claim 6, wherein the lower alkyl ether/ethers is/are selected from the group consisting of ethyleneglycol monomethyl ether, ethyleneglycol monoethyl ether, diethyleneglycol methyl ether, diethyleneglycol ethyl ether, triethyleneglycol monomethyl ether, and triethyleneglycol monoethyl ether.

15. The composition according to claim 6, wherein the nitrogen-containing compound/compounds is/are selected from the group consisting of 2-pyrrolidone and N-methyl-2-pyrrolidone.

16. The composition according to claim 6, wherein the sulfur-containing compound/compounds is/are selected from the group consisting of dimethyl sulfoxide, tetramethylenesulfone and thioglycol.

17. The composition according to claim 9, wherein the alcohol/alcohols is/are selected from the group consisting of methyl alcohol, ethyl alcohol, n-propyl alcohol, isopropyl alcohol, n-butyl alcohol, sec-butyl alcohol, t-butyl alcohol, and isobutyl alcohol.

18. The composition according to claim 9, wherein the ketone/ketones is/are selected from the group consisting of acetone, methylethyl ketone, and diacetone alcohol.

19. The composition according to claim 9, wherein the ester/esters is/are selected from the group consisting of ethyl acetate and ethyl lactate.

20. The composition according to claim 9, wherein the polyhydric alcohol/polyhydric alcohols is/are selected from the group consisting of ethyleneglycol, diethyleneglycol, triethyleneglycol, propyleneglycol, butyleneglycol, 1,4-butanediol, 1,2,4-butanetriol, 1,5-pentanediol, 1,2,6-hexanetriol, hexyleneglycol, glycerol, glycerol ethoxylate, and trimethylolpropane ethoxylate.

21. The composition according to claim 9, wherein the lower alkyl ether/ethers is/are selected from the group consisting of ethyleneglycol monomethyl ether, ethyleneglycol monoethyl ether, diethyleneglycol methyl ether, diethyleneglycol ethyl ether, triethyleneglycol monomethyl ether, and triethyleneglycol monoethyl ether.

22. The composition according to claim 9, wherein the nitrogen-containing compound/compounds is/are selected from the group consisting 2-pyrrolidone and N-methyl-2-pyrrolidone.

23. The composition according to claim 9, wherein the sulfur-containing compound/compounds is/are selected from the group consisting of dimethyl sulfoxide, tetramethylenesulfone and thioglycol.

24. The light resistant colorant according to claim 1, wherein the light resistant colorant is a compound represented by Formula 4:

Formula 4

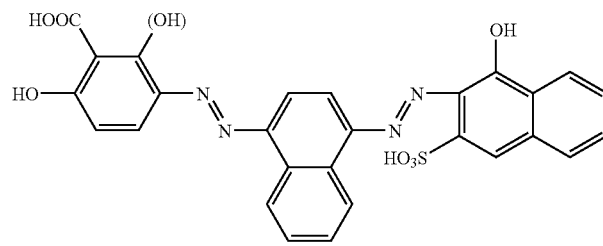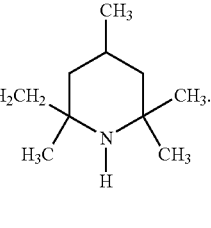

25. The light resistant colorant according to claim 1, wherein the light resistant colorant is a compound represented by Formula 6:

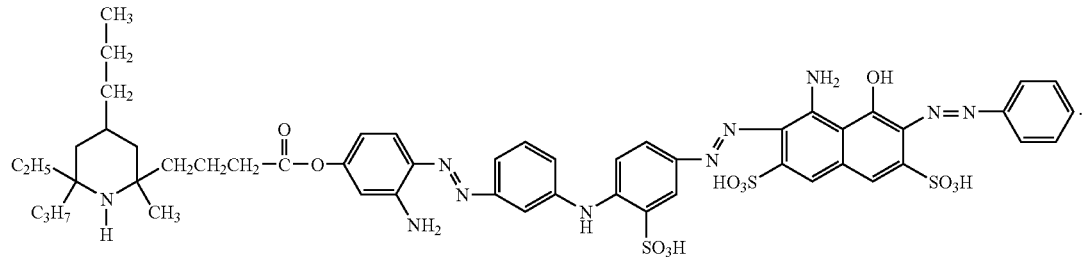

Formula 6

26. The light resistant colorant according to claim 1, wherein the light resistant colorant is a compound represented by Formula 7:

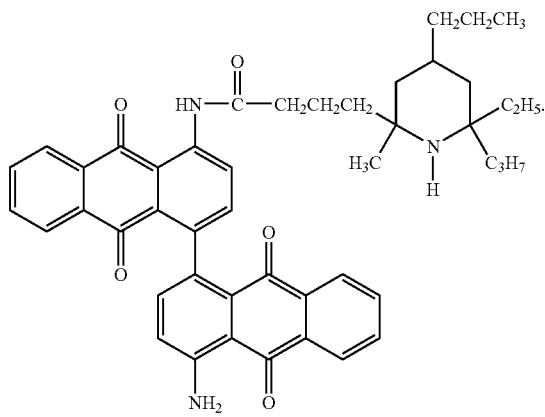

Formula 7

27. The light resistant colorant according to claim 1, wherein the light resistant colorant is a compound represented by Formula 9:

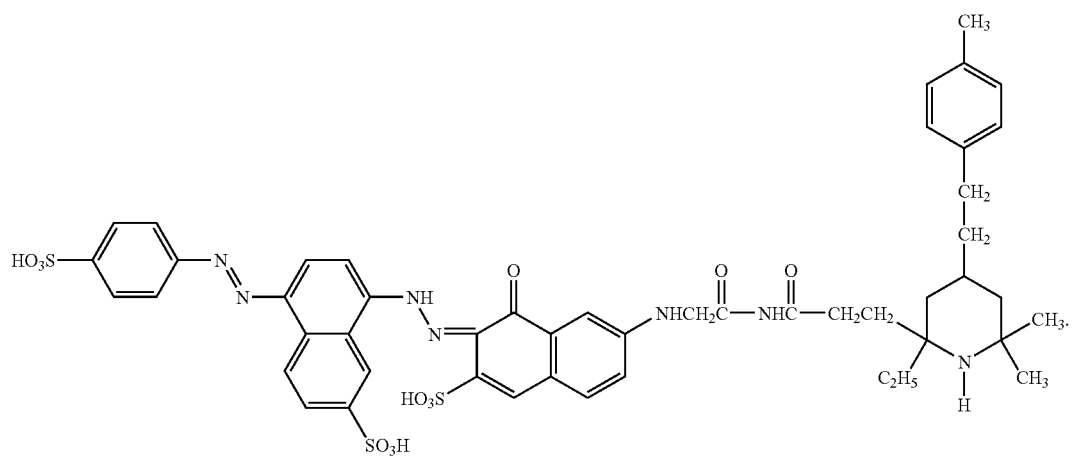

Formula 9

28. The light resistant colorant according to claim 1, wherein the light resistant colorant is a compound represented by Formula 11:

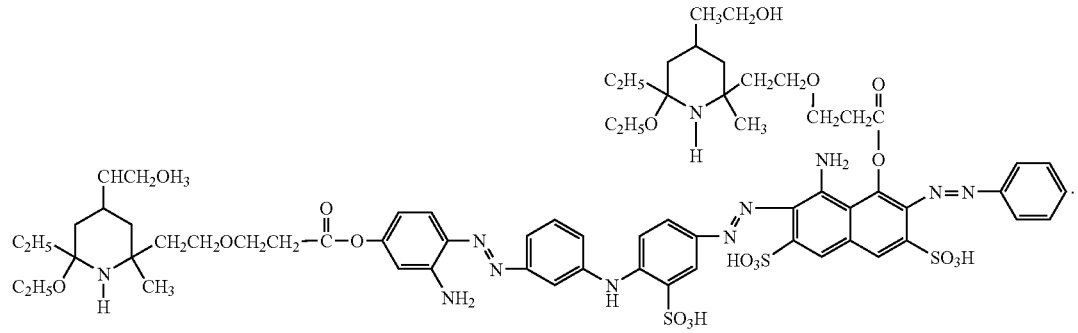
Formula 11
29. The light resistant colorant according to claim 1, wherein the light resistant colorant is a compound represented by Formula 13:
Formula 13
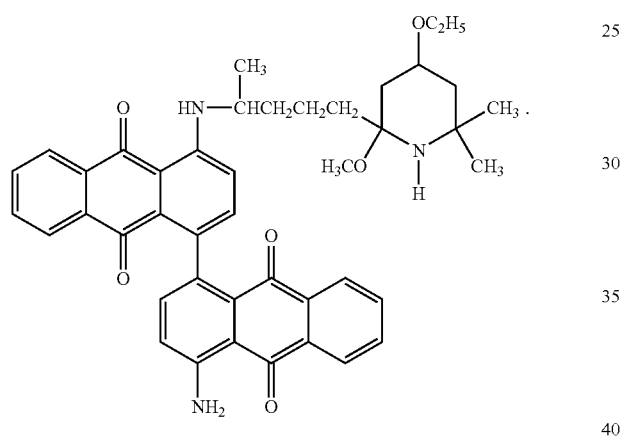
* * * * *

UNITED STATES PATENT AND TRADEMARK OFFICE
CERTIFICATE OF CORRECTION

| | | |
|---|---|---|
| PATENT NO. | : 7,064,210 B2 | Page 1 of 1 |
| APPLICATION NO. | : 10/672062 | |
| DATED | : June 20, 2006 | |
| INVENTOR(S) | : Yeon-kyoung Jung et al. | |

It is certified that error appears in the above-identified patent and that said Letters Patent is hereby corrected as shown below:

Column 18, Line 4, after "hydroxyl" delete "groups caroxyl" to --groups, carboxyl--.

Column 20, Line 39, after "consisting" insert --of--.

Signed and Sealed this

Twenty-eighth Day of November, 2006

JON W. DUDAS
*Director of the United States Patent and Trademark Office*